United States Patent [19]

Postle et al.

[11] 4,417,072
[45] Nov. 22, 1983

[54] HYDROQUINONE DERIVATIVES AND THEIR USE IN PHOTOGRAPHIC MATERIALS

[75] Inventors: Stephen R. Postle, Brentwood; Patrick D. P. Thomas, Chelmsford; Brian R. D. Whitear, Brentwood, all of England

[73] Assignee: Ciba-Geigy AG, Basel, Switzerland

[21] Appl. No.: 306,846

[22] Filed: Sep. 29, 1981

[30] Foreign Application Priority Data

Oct. 2, 1980 [GB] United Kingdom ............... 8031742

[51] Int. Cl.³ ................... C07C 69/80; C07C 69/82
[52] U.S. Cl. ..................... 560/86; 260/934; 260/946; 260/950; 430/438; 430/495; 546/261; 546/275; 546/283; 546/284; 546/294; 546/299; 546/322; 548/531; 548/536; 549/59; 549/60; 549/64; 549/71; 549/472; 549/485
[58] Field of Search ................ 560/11, 18, 52, 54, 560/86; 260/934, 946, 950, 326.35, 326.25, 326.36, 326.46, 347.4, 347.5; 546/261, 275, 283, 284, 299, 294, 322; 549/59, 60, 64, 71, 472, 485; 548/531, 536

[56] References Cited

U.S. PATENT DOCUMENTS

| | | | |
|---|---|---|---|
| 1,912,734 | 6/1933 | Staud et al. | 560/86 |
| 2,099,455 | 11/1937 | Strain | 560/86 X |
| 3,076,837 | 2/1963 | Mills | 560/86 |
| 3,962,314 | 6/1976 | Economy et al. | 560/86 X |

FOREIGN PATENT DOCUMENTS 350461 1/1961 Switzerland .
1290821 9/1972 United Kingdom .

OTHER PUBLICATIONS

Chemical Abstracts vol. 57:8479d,e 1962.

*Primary Examiner*—Natalie Trousof
*Assistant Examiner*—Vera C. Clarke
*Attorney, Agent, or Firm*—Joseph G. Kolodny

[57] ABSTRACT

Substituted hydroquinone compounds of the formula

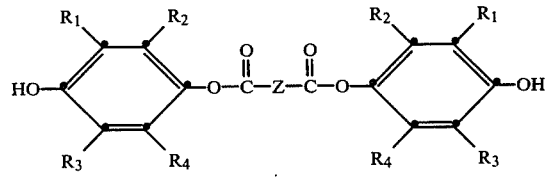

wherein $R_1$ to $R_4$ are hydrogen or alkyl and Z is an aromatic ring or a group of the formula —X—Y—X—, wherein X is an aromatic ring and Y is an electron withdrawing group, are incorporated as developers into photographic materials. These materials are suitable for activation processings.

6 Claims, No Drawings

HYDROQUINONE DERIVATIVES AND THEIR USE IN PHOTOGRAPHIC MATERIALS

The present invention relates to novel substituted hydroquinone derivatives and to their use in photographic material.

Hydroquinone is the most widely used developing agent for developing latent silver images in silver halide photographic material. Most usually exposed photographic material is processed in a bath containing hydroquinone to develop the latent image but for some types of processing it is preferable that the hydroquinone is present already in the photographic material which after exposure is processed in an alkaline bath to develop the latent image as hydroquinone only acts as a developing agent under alkaline conditions. Such as method of processing is known as activation processing. Activation processing is extremely rapid but is not widely employed except in certain special circumstances because the disadvantages of incorporating hydroquinone in the photographic material outweigh the advantages. These disadvantages include developer decomposition on ageing and interference with the setting and hardening of the gelatin or other colloidal layers in which it is incorporated during the coating of the photographic material. Further, activation processing often tends to cause stain and tanning of the processed material.

In an effort to overcome these disadvantages it has been proposed to use protected hydroquinones which are substituted hydroquinones in which the protecting group or groups are cleaved at the high pH value of the alkaline processing bath. However it has proved difficult to find substituted hydroquinones which are readily cleavable in the alkaline bath and thus which release the active hydroquinone quickly enough to achieve rapid processing and also substituted hydroquinones which are stable during coating and on storage of the photographic material. Many of the proposed substituted hydroquinone compounds contain in the protective moiety desensitising groups which limit the use of such compounds, or are coloured due to the presence of chromophoric groups, such as nitro groups, in the protective moiety. Such coloured compounds may be of use in certain circumstances but their presence tends to cause speed losses in the photographic material.

Some of the proposed hydroquinone derivatives are water-insoluble and these compounds comprise comparatively bulky water-insolubilising groups which lead to high coating weights. The presence of high molecular weight components in a layer of photographic material often leads to poor inter-layer or layer/base adhesion and poor layer hardening. Examples of water-insoluble hydroquinone derivatives are given in Research Disclosure 16444 of December 1977.

It has now been found a novel class of substituted hydroquinone compounds which are water-insoluble but which cleave rapidly in alkaline solution and which exhibit superior storage stability and little tendency to cause stain or tanning problems when material which contains them is activation processed. Furthermore, none of the compounds are coloured nor do they contain any densensitising groups, and all can be formulated easily in photographic layers.

According to the present invention there is provided a substituted hydroquinone compound of the formula

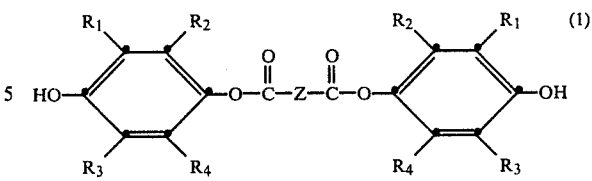

wherein $R_1$ to $R_4$ are each hydrogen or alkyl having from 1 to 4 carbon atoms, Z is an aromatic ring or is a group —X—Y—X— wherein X is an aromatic ring and Y is an electron withdrawing linking group.

In formula (1), $R_1$, $R_2$, $R_3$ and $R_4$ are each hydrogen or alkyl having 1 to 4 carbon atoms such as methyl, ethyl, propyl, butyl, and t-butyl. Preferably, $R_1$ to $R_4$ are each hydrogen, methyl or t-butyl. Most preferably, $R_1$ to $R_4$ each denote hydrogen.

Z stands for an monocyclic aromatic ring system. This ring system is preferably 5- or 6-membered and optionally contains hetero atoms such as nitrogen, oxygen or sulphur. Examples of suitable ring systems Z are furylene, thienylene, pyrrolylene, pyridinylene or phenylene. The 6-membered heterocyclic aromatic rings are preferred. Phenylene is mostly preferred.

Z denotes further a group of the formula —X—Y—X— wherein X is an aromatic ring system as described above for Z, and Y is an electron withdrawing linking group. Preferably X is phenylene and Y is e.g. —S$_2$—, —SO—, —CO— or =PO—A, wherein A denotes alkyl or alkoxy having from 1 to 4 carbon atoms such as methyl, ethyl, propyl, butyl, t-butyl and the corresponding alkoxy radicals, or A is aryl or aryloxy such as phenyl and phenoxy or A is a group of the formula

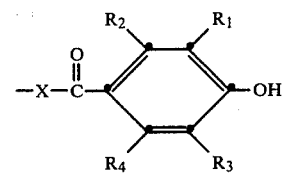

wherein $R_1$, $R_2$, $R_3$, $R_4$ and X have the meanings assigned to them above.

Preferably, Y is —SO$_2$—, —SO— or —CO—. Most preferably, Y is —SO$_2$—.

Another object of the present invention relates to a method for the manufacture of the compounds of formula (1).

According to another aspect of the present invention there is provided photographic silver halide material which comprises on a support at least one colloid silver halide layer and at least one colloid layer which comprises at least one substituted hydroquinone compound of formula (1).

Another object of the present invention is a process for the manufacture of this photographic material.

Compounds of formula (1) may be prepared by reacting 1 mole of an acid chloride of formula

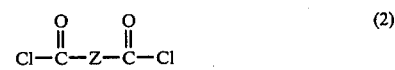

where Z has the meaning assigned to it above with 2 moles of a hydroquinone of formula

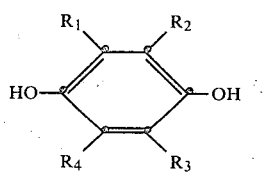

where $R_1$ to $R_4$ have the meanings assigned to them above in the presence of an organic solvent and a base.

Suitable solvents include e.g. acetone, acetonitrile and methylene chloride.

Suitable bases include e.g. pyridine and triethylamine.

Alternatively the compounds of formula (1) may be prepared using a Schotten-Baumann reaction wherein the hydroquinone compound of formula (3) dissolved in aqueous sodium carbonate solution is reacted with the acid chloride of formula (2) in an aqueous medium.

This latter reaction procedure may be employed even when the acid chloride of formula (2) is water-insoluble.

Usually silver halide photographic material which is to be activation processed comprises only one silver halide colloid layer and most usually this colloid is gelatin.

Therefore according to a preferred embodiment of this aspect of the present invention there is provided photographic silver halide material which comprises coated on a support at least one colloid silver halide layer which comprises at least one substituted hydroquinone of formula (1).

Preferably, the colloid silver halide layer is a gelatino silver halide layer. This layer preferably comprises a substituted hydroquinone of formula (1).

The amount of the compound of the formula (1) present in the silver halide photographic material will depend on the actual compound used and on the proposed use of the photographic material. Preferably however the compound of formula (1) is present in the photographic material in an amount within the range of 0.1 to 1.0 moles per 1.5 moles of silver halide present in the photographic material.

Preferably the substituted hydroquinone of formula (1) are dispersed in the layer of the photographic material as a solid dispersion which has been obtained by ball-milling the solid in an aqueous medium in the presence of a wetting agent. Alternatively the water-insoluble compounds of formula (1) may be dispersed in the layer of the photographic material in an oil, for example tricresyl phosphate.

The silver halide present in the photographic material may be any one of the normally employed silver halides such as silver chloride, silver bromide, silver chlorobromide, silver bromoiodide and silver iodochlorobromide.

The silver halide emulsions may be optically sensitised by the presence therein of optical sensitising dyes, for example merocyanine or carbocyanine dyes.

The silver halide emulsions may contain any of the additives commonly used in photographic emulsions, for example wetting agents such as polyalkylene oxides, stabilising agents such as tetraazaindenes, metal sequestering agents and growth or crystal habit modifying agents commonly used for silver halide, such as adenine.

Preferably the colloid medium is gelatin or a mixture of gelatin and a water-soluble latex, for example a latex vinyl acrylate-containing polymer. Most preferably if such a latex is present in the final emulsion it is added after all crystal growth has occurred. However, other water-soluble colloids, for example casein, polyvinylpyrrolidine or polyvinyl alcohol, may be used alone or together with gelatin.

The support may be any one of the supports normally used for photographic materials including paper base, polyethylene-coated paper base, oriented and subbed polyethylene terephthalate, cellulose triacetate, cellulose acetate butyrate, polystyrene and polycarbonate.

The photographic material of the present invention may be used in a large number of different ways including black and white print material, X-ray film material, colour film material, microfilm products and direct positive material.

The photographic material of the present invention most usually is prepared by forming an aqueous colloid coating solution of the silver halide which comprises either a dispersion of the compound of formula (1) or a solution of the compound of formula (1) and this colloid coating solution is coated as a layer on a support and dried.

After exposure the photographic material may be treated with an activator solution which is an aqueous alkaline solution which comprises for example sodium hydroxide or sodium carbonate. Most usually the activator solution will have a pH value of between 10 and 14. Stabilizers, antifoggants and development accelerators may also be present in the activator solutions.

The activator solutions may be applied to the exposed photographic material according to the present invention in all the usual ways such as surface application, total immersion of the material in the activator solution and spraying.

After the inventive photographic material has been activator processed it may be fixed in a silver halide fixing solution, for example ammonium thiosulphate, to remove the undeveloped silver halide, or it may be stabilised to render the remaining silver halide light-sensitive by treatment with a known stabiliser treatment solution, for example an aqueous ammonium thiocyanate solution.

The following Examples will serve to illustrate the invention.

EXAMPLE I

Preparation of the compound of the formula

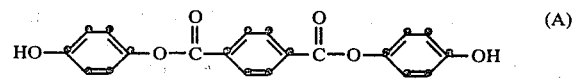

Hydroquinone (2.2 g) is stirred in acetone (10 ml) and pyridine (1.6 ml) and treated over 5 minutes with terephthaloyl chloride (2.03 g) in acetone (15 ml) with icewater cooling. Acetone (7 ml) is added to give a stirrable mixture, and after a further 30 minutes the mixture is filtered and the solid bis-ester washed with water and dried to give a white solid (2.28 g). M.p. 305°–310° C.

Compounds (B), (C), (D) and (E) are prepared similarly using the appropriate acid chloride.

| Compound | M.p. [°C.] |
|---|---|
| (B) [structure: bis(4-hydroxyphenyl) phthalate] | 123–125 |
| (C) [structure with furan-2,5-dicarboxylate bis(4-hydroxyphenyl) ester] | 228–232 |
| (D) [structure with pyridine-2,6-dicarboxylate bis(4-hydroxyphenyl) ester] | 230–232 |
| (E) [structure with sulfone linkage] | >310 |

Also prepared are the following prior art compounds

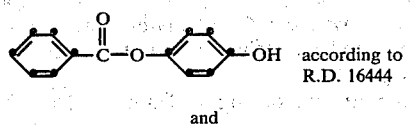  (F) according to R.D. 16444 and

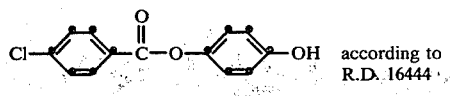  (G) according to R.D. 16444

EXAMPLE II

Preparation of solid dispersion of compound (A).
The following mixture is prepared:
1 g compound (A)
10 ml distilled water
0.25 ml 30% anionic wetting agent
50 ml 2 mm glass beads The above ingredients are added to a 100 ml beaker and bead milling is effected by agitating the glass beads with a propeller rotating at 1000 r.p.m. for 24 hours. At the end of this time the glass beads are removed by filtration.

Coatings of the dispersed compound (A) are prepared as follows:

10 ml aliquots of coating solution are made up according to the formula:
2 ml solid dispersion (prepared as described above)
0.90 ml silver chlorobromide emulsion (25 mg silver/dm$^2$)
0.50 ml 10% gel (decationised blend)
1 ml 1% aqueous formaldehyde solution
0.15 ml 1% anionic wetting agent
0.15 ml 1% nonionic wetting agent
Water to 10 ml The anionic wetting agent is an adduct of nonylphenol and 8 moles of ethylene oxide, esterified with sulfuric acid.

The nonionic wetting agent is an adduct of octylphenol and 10 moles of ethylene oxide.

The solution is coated at 40° C. on triacetate base attached to a glass plate, set at 5° C. and dried.

| | |
|---|---|
| Overall silver coating weight | 25 mg/dm$^2$ |
| Overall gel coating weight | 80 mg/dm$^2$ |
| Overall Compound (A) coating weight | 285 mg/dm$^2$ |

Similar coatings of compounds (B) to (G) are also prepared.

EXAMPLE III

All the coatings with compounds (A),(B),(C),(E),(F) and (G) are exposed in an overall manner. The coatings are treated with an activator solution comprising aqueous 2 n NaOH for 10 seconds in a bath, washed, fixed in an ammonium thiosulphate (82 g/l) fox for 2 minutes in a bath, washed and then dried. The silver densities obtained by this method for the various coatings are tabulated below.

TABLE 1

| Compound | D max |
|---|---|
| (A) | 2.20 |
| (B) | 3.89 |
| (C) | 2.73 |
| (D) | 2.82 |
| (E) | 2.88 |
| (F) | 0.59 (R.D. 16444) |
| (G) | 0.10 (R.D. 16444) |

The results of Table 1 show that the compounds of the present invention are superior to those hitherto known in the insoluble incorporated developer field. It is obviously important that the latent solubility of the protected developer in base should be as rapid as possible, and this is achieved in the invention compounds by the releasable protecting groups being of small bulk yet being rapidly cleaved in the presence of a base.

EXAMPLE IV

Coatings of compounds (A), (B), (C), (D), (E), (F) and (G) are made up as described in Example II, exposed imagewise and processed in an activator solution comprising 2 n NaOH for both 5 and 20 seconds. After the appropriate washing, fixing and drying stages the following results are obtained.

TABLE 2

| Compound | 5 seconds activation | | 20 seconds activation | |
|---|---|---|---|---|
| | D min | D max | D min | D max |
| (A) | 0.27 | 1.23 | 0.74 | 1.60 |
| (B) | 0.10 | 2.27 | 0.24 | 2.32 |
| (C) | 0.09 | 1.02 | 0.40 | 1.77 |
| (D) | 0.14 | 1.92 | 0.59 | 2.53 |
| (E) | 0.34 | 1.71 | 0.36 | 2.57 |
| (F) | 0.03 | 0.06 | 0.35 | 1.37 |
| (G) | 0.00 | 0.00 | 0.00 | 0.10 |

The results show the much higher D max values which may be obtained on both short and long processing times by use of the compounds of the present invention. Suppression of D min values by use of antifoggants is available by methods well known so that high D min values are not disadvantageous.

We claim:

1. A substituted hydroquinone compound of formula

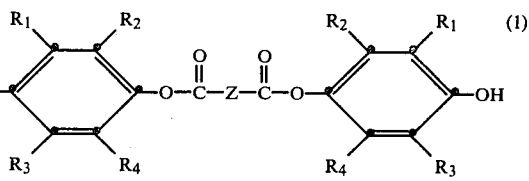

wherein $R_1$ to $R_4$ are each hydrogen or alkyl having from 1 to 4 carbon atoms, Z is an aromatic ring selected from the group consisting of furylene, thienylene, pyrrolylene, pyridinylene or 1,2- or 1,4-phenylene or is a group Z—Y—Z wherein Z is an aromatic ring as defined above and Y is —SO$_2$—, —SO—, —CO— or a group of the formula =PO—A, wherein A is alkyl or alkoxy each having 1 to 4 carbon atoms, phenyl, phenoxy or a group of the formula

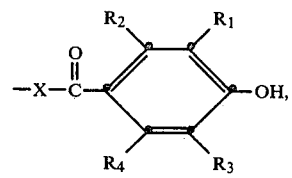

wherein $R_1$ to $R_4$ and Z are as defined above.

2. A compound according to claim 1, wherein $R_1$ to $R_4$ are each hydrogen, methyl or t-butyl.

3. A compound according to claim 2 wherein each of $R_1$ to $R_4$ are hydrogen.

4. A compound according to claim 1 wherein $R_1$ to $R_4$ are hydrogen and Z is 1,2- or 1,4-phenylene, furylene, pyridinylene or a group of the formula —Z—Y—Z—, wherein Z is phenylene and Y is —SO$_2$.

5. A compound according to claim 1 wherein Z is 1,2- or 1,4-phenylene.

6. A compound according to claim 1 having the formula

* * * * *